United States Patent
Mukohzaka

[19]
[11] Patent Number: 5,910,999
[45] Date of Patent: Jun. 8, 1999

[54] INDIVIDUAL IDENTIFICATION APPARATUS BASED ON FREQUENCY DOMAIN CORRELATION OF PLURAL REFERENCE IMAGES AND A TARGET IMAGE

[75] Inventor: Naohisa Mukohzaka, Hamamatsu, Japan

[73] Assignee: Hamamatsu Photonics K.K., Shizuoka-ken, Japan

[21] Appl. No.: 08/754,262

[22] Filed: Nov. 20, 1996

[30] Foreign Application Priority Data

Nov. 20, 1995 [JP] Japan .................................. 7-325033

[51] Int. Cl.⁶ .................................................. G06K 9/00
[52] U.S. Cl. .......................... 382/124; 382/278; 382/280
[58] Field of Search .................................. 382/115, 116, 382/118, 124, 125, 126, 127, 278, 280; 356/71, 390, 392; 340/825.34; 364/728.07, 728.03, 726.02

[56] References Cited

U.S. PATENT DOCUMENTS

| 5,050,220 | 9/1991 | Marsh et al. |
| 5,485,312 | 1/1996 | Horner et al. ........................... 359/561 |
| 5,613,013 | 3/1997 | Schuette ................................. 382/124 |
| 5,761,330 | 6/1998 | Stoianov et al. ........................ 382/127 |

FOREIGN PATENT DOCUMENTS

| 54-12064 | 5/1979 | Japan ............................... G06K 9/00 |
| 59-32081 | 2/1984 | Japan ............................... G06K 9/76 |
| 5-159056 | 6/1993 | Japan ............................... G06F 15/70 |
| 2 270 586 | 3/1994 | United Kingdom ............ A61B 5/117 |

Primary Examiner—Jose L. Couso
Assistant Examiner—Brian P. Werner
Attorney, Agent, or Firm—Sughrue, Mion, Zinn, Macpeak & Seas, PLLC

[57] ABSTRACT

The image pick up portion 50 picks up a pattern of a predetermined body portion of a specific individual a plurality of times and outputs a plurality of reference image signals for being stored. The image pick up portion 50 also picks up a pattern of the predetermined body portion of an arbitrary individual desired to be identified with the specific individual and outputs a target image signal. The calculation processing portion 60 electronically performs a Fourier transform on the plurality of reference image signals and the target image signal. The calculation processing portion 60 superimposes the Fourier transformed results of the plurality of reference image signals. The calculation processing portion electronically multiplies the thus superimposed reference image signals with the Fourier transformed target image signal. The calculation processing portion electronically performs an inverse Fourier transform on the multiplied results to thereby obtain a similarity degree between the reference image signals and the target image signal, thereby judging whether or not the arbitrary individual is the specific individual.

22 Claims, 3 Drawing Sheets

1

INDIVIDUAL IDENTIFICATION APPARATUS BASED ON FREQUENCY DOMAIN CORRELATION OF PLURAL REFERENCE IMAGES AND A TARGET IMAGE

BACKGROUND OF THE INVENTION

1. Field of the Invention

The present invention relates to an individual identification apparatus for confirming identities of individuals by using a pattern recognition technique.

2. Description of the Related Art

Recently, confirmation of identities of individuals is required in order to manage entrance and exit of individuals in and out of restricted areas and to prevent free access to important equipment. An individual identification apparatus has been proposed to identify each individual attempting access, and so under investigation, with a specific individual on record. The person under investigation will be referred to as an "arbitrary individual" hereinafter. Patterns of certain body portions, such as fingerprints, face patterns, retinal vascular patterns, palm prints, voice patterns, and DNA patterns are unique for each individual. Accordingly, the individual identification apparatus is designed to previously record a pattern of such a unique feature of a specific individual. This feature of the specific individual will be referred to as a reference pattern hereinafter. When desiring to identify an arbitrary individual with the specific individual, the device picks up a corresponding pattern of the arbitrary person. The pattern of the arbitrary person will be referred to as a target pattern hereinafter. Then, the individual identification apparatus compares the picked up target pattern with the recorded reference pattern.

SUMMARY OF THE INVENTION

It is conceivable that an image correlation calculation is performed on the target pattern and the reference pattern. A correlation peak is obtained and the highest value of the peak is detected. Match or mismatch between the target pattern and the reference pattern is determined based on the highest value of the correlation peak. A highly accurate pattern recognition operation can be achieved through the above-described image correlation calculation.

There is a possibility, however, that the target pattern will be picked up while being distorted from its normal shape. For example, a fingerprint might be warped or smudged when picked up. Also, although the reference pattern is picked up at a standard posture and recorded in the apparatus, there is also a possibility that the target pattern will be shifted or rotated from the standard posture when it is picked up. In these cases, the image correlation obtained between the target pattern and the reference pattern will have a low value even though the arbitrary person and the specific person are actually the same individual. A mistaken or false rejection ratio will increase.

In order to make the apparatus flexible enough to allow for some distortion or rotation of the target pattern, it is conceivable to previously record a plurality of reference patterns for the specific person's characteristic. In one conceivable method, when a target pattern of the arbitrary person is picked up, correlation calculations are performed between the target pattern and all the reference patterns. The highest values of the obtained correlation peaks are compared with a predetermined threshold value. When at least one correlation peak highest value is higher than the threshold value, the arbitrary person is determined as identical with the specific person. However, this method would take a long period of time to obtain the final judgement.

In order to solve this problem, information on reference filters, which record the reference patterns, may be superimposed to produce a multiple filter. For example, reference pattern candidates, picked up from a specific person, can be optimized through repeatedly calculating correlations between the reference pattern candidates and a plurality of patterns previously picked up from the same specific person. Thus optimized pattern candidate is then recorded as a reference filter.

It is noted, however, that in order to optimize the filter, the correlation calculation has to be performed a plurality of times. Therefore, the optimizing calculation and consequently the entire recordation process are time consuming.

In another conceivable method, an optical correlation calculation can be performed by exposing a film to the specific person's pattern multiple times to produce a Fourier-transformed hologram having a multiple pattern of the specific person.

It is very difficult, however, to accurately arrange an optical system to achieve the multiple exposure operation. Accordingly, the different views of the specific person's pattern may not be accurately superimposed one on another. It is impossible to perform an accurate individual's recognition operation with an inaccurately-produced multiple filter. In order to solve this problem, it is conceivable that the multiple exposure be achieved while changing the angle between a reference light ray and an object light ray. Alternatively, the multiple exposure may be attained while changing the wavelengths of the exposing light rays. These methods, however, require providing an angle adjusting device or a wavelength adjusting device in addition to the optical correlation-achieving optical system, thereby increasing the overall size of the individual identification device.

It is an object of the present invention to overcome the above-described drawbacks and to provide an improved individual identification apparatus capable of performing a highly accurate recognition operation even on a rotated or distorted pattern and of recording the specific person's pattern within a short period of time.

In order to attain the above and other objects, the present invention provides an individual identification apparatus for identifying an arbitrary individual with a specific individual, the apparatus comprising: image pick up means for picking up a pattern of a predetermined body portion of a specific individual a plurality of times and for outputting a plurality of reference image signals for being stored, the image pick up means also picking up a pattern of the predetermined body portion of an arbitrary individual desired to be identified with the specific individual and for outputting a target image signal; and calculation processing means for electronically performing a Fourier transform on the plurality of reference image signals and the target image signal, for superimposing the Fourier transformed results of the plurality of reference image signals, for electronically multiplying the superimposed reference image signals with the Fourier transformed target image signal, and for electronically performing an inverse Fourier transform on the multiplied results to thereby obtain a similarity degree output indicative of similarity between the reference image signals and the target image signal, thereby judging whether or not the arbitrary individual and the specific individual are the same individual.

BRIEF DESCRIPTION OF THE DRAWINGS

The above and other objects, features and advantages of the invention will become more apparent from reading the following description of the preferred embodiment taken in connection with the accompanying drawings in which.

DETAILED DESCRIPTION OF THE PREFERRED EMBODIMENT

Figure 1:
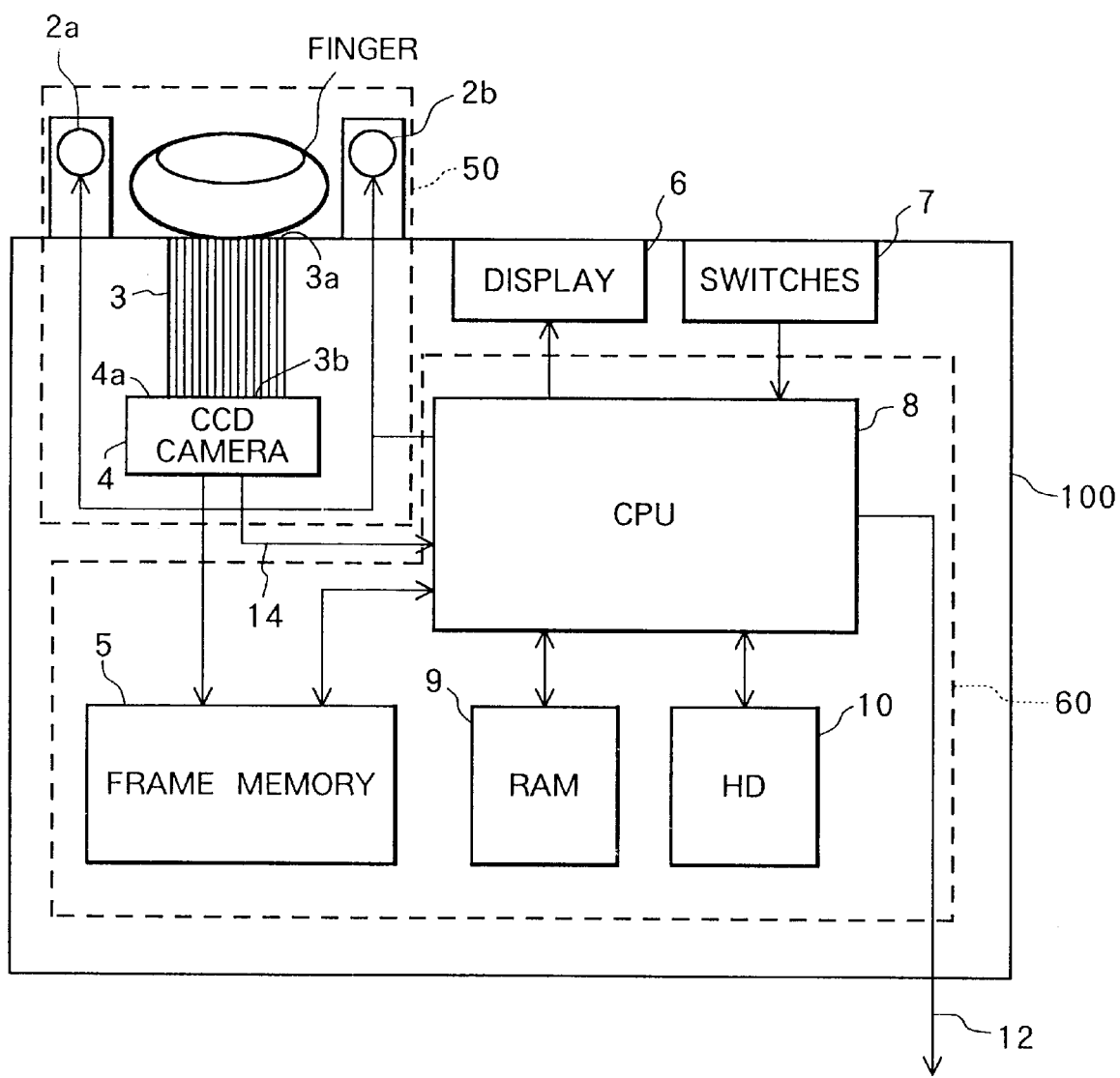
FIG. 1 is a block diagram showing a configuration of an individual identification apparatus according to an embodiment of the present invention.

An individual identification apparatus according to a preferred embodiment of the present invention will be described while referring to the accompanying drawings wherein like parts and components are designated by the same reference numerals.

FIG. 1 shows the overall configuration of the individual identification apparatus 100 of the present embodiment. The apparatus 100 of the present embodiment is for identifying an individual under investigation (arbitrary individual) with a specific individual on file. In order to confirm whether or not the arbitrary person and the specific person are the same individual, the apparatus picks up a fingerprint of the arbitrary person and electronically calculates a correlation between the arbitrary individual's fingerprint and a fingerprint of the specific individual previously recorded in the apparatus. The apparatus judges whether or not the arbitrary person and the specific person are the same individual based on the correlation.

As shown in FIG. 1, the individual identification apparatus 100 includes: an image pick-up portion 50; a calculation processing portion 60; a display portion 6; and switches 7. The image pick-up portion 50 includes a pair of light emission diodes (LEDs) 2a and 2b, a fiber optical plate (FOP) 3, and a charge-coupled device (CCD) camera 4.

The calculation processing portion 60 includes a frame memory 5, a CPU 8, a random access memory (RAM) 9, and a hard disk (HD) 10. The display portion 6 is for showing recognition results. The switches 7 include several switches with which an operator controls the apparatus 100. The switches include mode setting keys for setting a filter storage mode, a recognition mode, and a pattern pick up mode. The switches further include a numerical pad for designating an identification number of a specific individual under investigation.

Next, the structure of the image pick up portion 50 will be described in greater detail.

The pair of LEDs 2a and 2b are light emitting elements for irradiating with light a finger of an individual when desiring to pick up a fingerprint of the individual. The FOP 3 is an integrated bundle of a plurality of optical fibers. The FOP 3 has opposite end surfaces, that is, an input end surface 3a and an output end surface 3b, at the longitudinal ends of the optical fibers. The finger of the individual is placed on the input end surface 3a. The output end surface 3b contacts a light receiving surface 4a of the CCD camera 4. The FOP 3 transmits an image of the fingerprint from the input end surface 3a to the output end surface 3b. The CCD camera 4 serves as a two-dimensional image pick-up element for picking up the fingerprint outputted from the output end surface 3b.

The configuration of the calculation processing portion 60 will be described below.

The frame memory 5 is connected to the CCD camera 4, and serves as an image storage device for receiving image signals outputted from the CCD camera 4, digitizing the image signals, and then storing the digitized image signals. The CPU 8 is for performing various digital calculations, such as a fast Fourier transform (FFT) calculation, on the digital image signals stored in the frame memory 5 to thereby obtain a correlation signal indicative of a correlation between the specific individuals fingerprint and the arbitrary person's fingerprint. The CPU 8 is also for determining, based on the correlation signal, whether or not the arbitrary individual and the specific individual are the same individual. The CPU 8 is also for receiving instruction signals inputted from the switches 7, driving the LEDs 2a and 2b, and controlling the display 6 to show the determined results. The CPU 8 may be provided with an internal digital signal processor (DSP) for performing the enormous amounts of calculation such as the FFT calculation. Each of the RAM 9 and the HD 10 is for storing a filter image (matched filter) representative of the specific individual's fingerprint and an identification number indicative of the specific individual.

Figure 2:
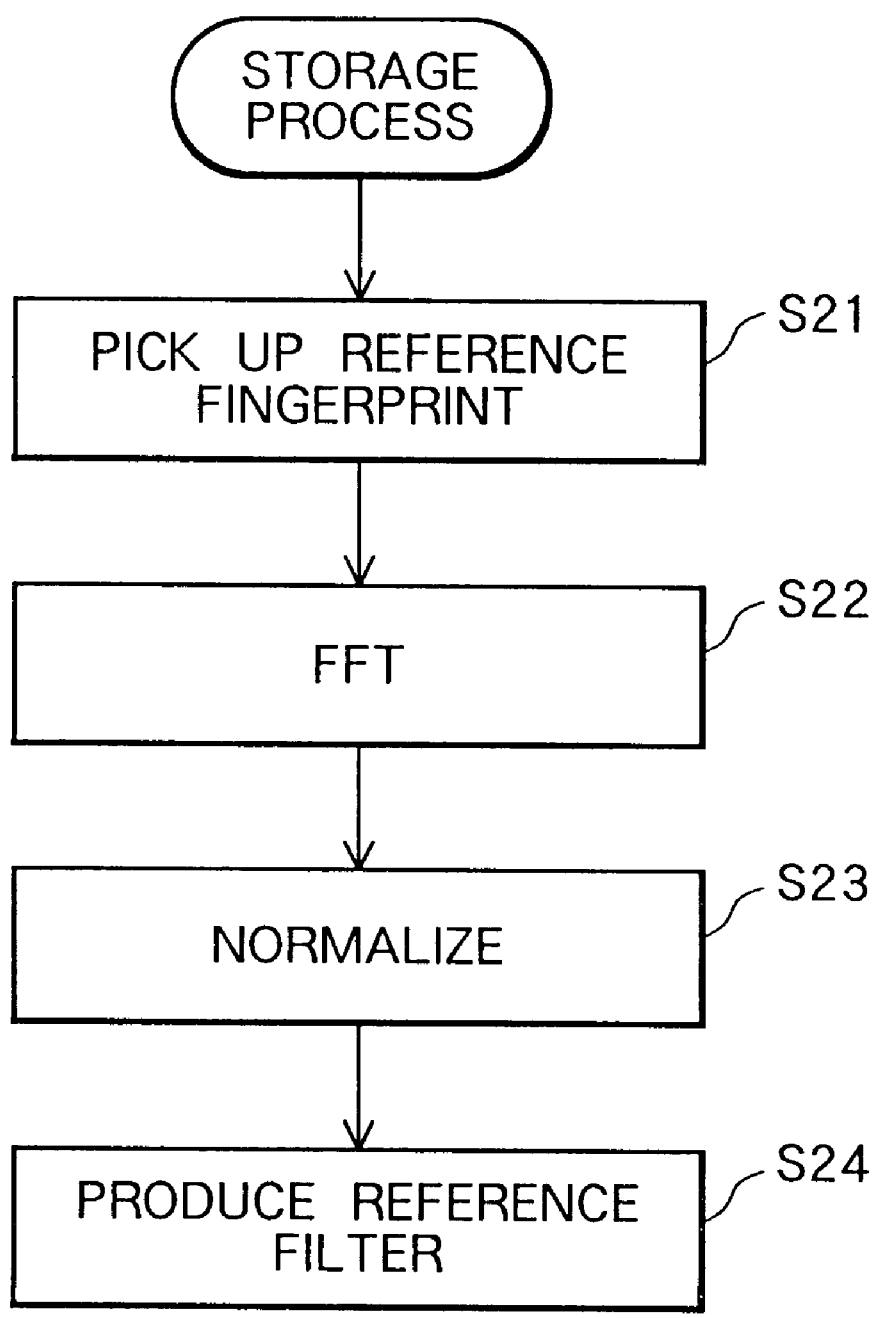
FIG. 2 is a flowchart representing a reference fingerprint storage process of the individual identification apparatus.
Figure 3:
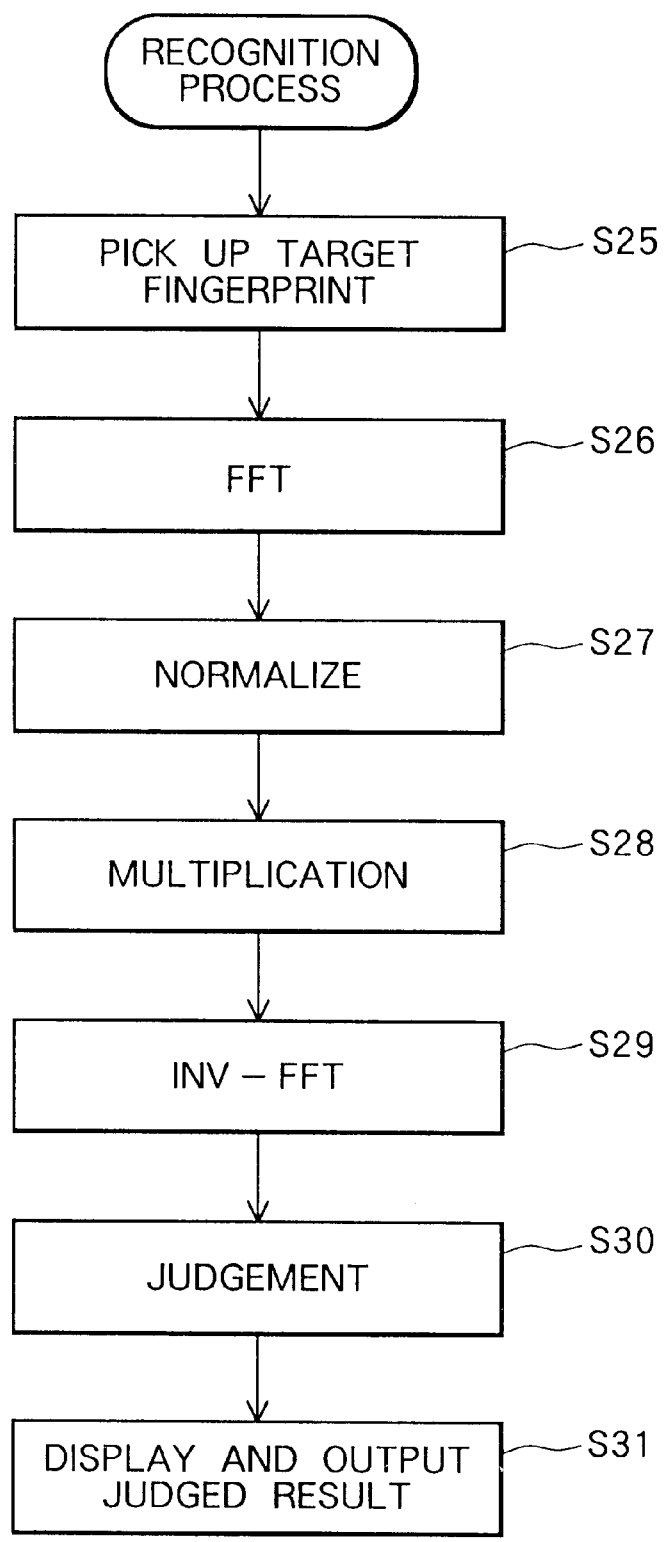
FIG. 3 is a flowchart representing an individual identification process of the individual identification apparatus.

According to the apparatus 100 with the above-described structure, a fingerprint of a specific individual is previously stored in the apparatus 100 through a filter storage process represented by the flowchart of FIG. 2. When desiring to know whether or not an arbitrary individual and the specific individual are the same individual, a recognition (individual identification) process is conducted as represented by the flowchart of FIG. 3.

The filter storage process will be first described with reference to FIG. 2.

When a specific individual desires to record his/her fingerprint in the apparatus 100, the specific individual first manipulates the mode setting key on the switches 7 to select a filter storage mode, whereupon the filter storage process starts. Then, the specific individual manipulates the numeric pad in the switches 7 to designate his/her own identification number, i.e., a so-called PIN-number (Personal Identification Number) of the specific individual. The specific individual places his/her finger on the input end surface 3a as shown in FIG. 1. Then, the specific individual again manipulates the mode setting key to select a pattern pick up mode, upon which the CPU 8 turns on the LEDs 2a and 2b in S21. As a result, a fingerprint image is formed on the output end surface 3b of the FOP 3. The fingerprint image is picked up by the CCD camera 4. This fingerprint image will be referred to as a "reference fingerprint" hereinafter. The reference fingerprint is then digitized by the frame memory 5 and stored in the frame memory 5.

In S21, the above-described reference fingerprint-getting operations are performed several times, for example, four times. It is noted that the specific person has to place his/her finger on the FOP 3 in four different manners. As a result, four different reference fingerprints A, B, C, and D are stored in the frame memory 5 for the same specific person. Thus, a plurality of (four, in this example) reference fingerprints are stored for the single specific person in order to enhance flexibility of the apparatus 100 enough to allow for possible distortions or rotations of the target pattern on the FOP 3 during the recognition process as described later.

Next, in S22, the CPU 8 performs a fast Fourier transform (FFT) operation on the four reference fingerprints A, B, C, and D which are now stored in the frame memory 5. Thus obtained Fourier transformed patterns, $REF_A$, $REF_B$, $REF_C$, and $REF_D$ of the reference fingerprints A, B, C, and D are represented by the following complex indications (1):

$$REF_A = X_A + Y_A j,$$
$$REF_B = X_B + Y_B j,$$
$$REF_C = X_C + Y_C j$$
$$REF_D = X_D + Y_D j \qquad (1)$$

wherein:

$X_A$ through $X_D$ are real parts of the Fourier transformed results of the reference fingerprints A, B, C, and D; and $Y_A$ through $Y_D$ are imaginary parts of the Fourier transformed results of the reference fingerprints A, B, C, and D.

Each of the expressions (1) is a matrix expression because each of the reference fingerprints A through D is two-dimensional image. When each reference fingerprint has a size of N×N dots (pixels), for example, then each of the values $X_A$ through $X_D$ and $Y_A$ through $Y_D$ is a matrix consisting of N×N values.

It is noted that an arbitrary person's fingerprint will also be represented in a similar manner to be described later.

Then, in S23, the CPU 8 normalizes, into one (1), the amplitude terms of the Fourier transformed images $REF_A$, $REF_B$, $REF_C$, and $REF_D$, to thereby produce phase-only patterns $REFpo_A$, $REFpo_B$, $REFpo_C$, and $REFpo_D$. Each phase-only pattern REFpo ($REFpo_A$, $REFpo_B$, $REFpo_C$, or $REFpo_D$) can be expressed by the corresponding Fourier-transformed reference fingerprint REF ($REF_A$, $REF_B$, $REF_C$, or $REF_D$) (=X+Y·j) through the following formulas (2):

$$REFpo = X/(X^2+Y^2)^{1/2} + \{Y/(X^2+Y^2)^{1/2}\}j$$
$$= X' + Y'j$$

$$amplitude = (X'^2 + Y'^2)^{1/2} = 1$$
$$phase = \tan^{-1}(Y'/X') = \tan^{-1}(Y/X) \qquad (2)$$

The CPU 8 further normalizes each phase-only pattern REFpo ($REFpo_A$, $REFpo_B$, $REFpo_C$, or $REFpo_D$) so that a power spectrum of the phase-only pattern will have a fixed total amount. This normalization operation is performed in order that a highest value of a correlation peak, which will be obtained through the recognition process of FIG. 3, can be compared with a certain threshold value under a predetermined and fixed condition. Even though the above-described phase-only operation normalizes the amplitude term of each phase-only pattern REFpo ($REFpo_A$, $REFpo_B$, $REFpo_C$, or $REFpo_D$), there is still a possibility that the total amount in the power spectrum of the phase-only pattern REFpo will vary when subjected to additional pattern processing during the recognition operation. In view of this, it is preferable that the power spectrum total amount be normalized into a certain fixed value except when no additional pattern processing will be performed during the recognition operation.

According to this embodiment, because each original reference pattern has the size of N×N dots (pixels), each phase-only pattern REFpo ($REFpo_A$, $REFpo_B$, $REFpo_C$, or $REFpo_D$) is normalized so that the phase-only pattern will have a power spectrum with its total amount being equal to a value of $N^2$ (=N×N).

The power spectrum-normalized phase-only pattern REF"po (REF"$po_A$, REF"$po_B$, REF"$po_C$, or REF"$po_D$) can be expressed by the following formula (3):

$$REF''po = \frac{X' \times (N \times N)}{REFsum} + \frac{Y' \times (N \times N)}{REFsum} j = X'' + Y'' j \qquad (3)$$

where $$REFsum = \sum_{n=1, m=1}^{N,N} \sqrt{(X_{nm}^2 + Y_{nm}^2)}$$

It is noted that the normalized phase-only pattern REF"po will have a power spectrum with its total amount being fixed to the value $N^2$ as expressed by the following formula (4):

$$\sum_{n=1,m=1}^{N,N} \sqrt{\left[\left(\frac{X_{nm} \times N^2}{REFsum}\right)^2 + \left(\frac{Y_{nm} \times N^2}{REFsum}\right)^2\right]} \qquad (4)$$
$$= \frac{N^2}{REFsum} \sum_{n=1,m=1}^{N,N} \sqrt{(X_{nm}^2 + Y_{nm}^2)}$$
$$= \frac{N^2}{REFsum} \times REFsum$$
$$= N^2$$

Because the phase-only pattern REF"po is normalized to have the fixed power spectrum total amount, an autocorrelation, obtained through the recognition operation of FIG. 3, will always have a fixed value. As will be described later, the recognition operation of FIG. 3 is designed so that a highest value of a correlation peak, obtained through the recognition operation, is compared with a maximum value of cross-correlation peaks obtained for a number of different people. Because the phase-only pattern REF"po has the fixed total amount of a power spectrum, the comparing operation can be always performed under a fixed condition so that stable individual recognition can be attained.

Then, in S24, the CPU 8 adds all the normalized phase-only patterns REF"$po_A$, REF"$po_B$, REF"$po_C$, and REF"$po_D$ into a multiple filter Multi. Then, the CPU 8 calculates a (phase) conjugate Multi* of the superimposed patterns. Thus, the CPU 8 obtains a reference filter Multi* in which the four reference fingerprints are superimposed one on another.

The patterns Multi and Multi* can be expressed by the following formulas (5):

$$Multi = REF''po_A + REF''po_B + REF''po_C + REF''po_D \qquad (5)$$
$$= (X_A'' + Y_A''j) + (X_B'' + Y_B''j) +$$
$$(X_C'' + Y_C''j) + (X_D'' + Y_D''j)$$
$$= (X_A'' + X_B'' + X_C'' + X_D'') +$$
$$(Y_A'' + Y_B'' + Y_C'' + Y_D'')j$$
$$= X_M + Y_M j$$
$$Multi^* = X_M - Y_M j$$

Then, the CPU 8 stores, in each of the RAM 9 and the HD 10, the reference filter Multi* and the specific person's designated identification number.

Next, the recognition (individual identification) process will be described with reference to FIG. 3.

When an arbitrary person desires to be identified with the specific individual on record, the arbitrary person first manipulates the mode setting key to select the recognition mode, whereupon the recognition process of FIG. 3 starts. Then, the arbitrary person manipulates the numeric pad in the switches 7 to designate the identification number of the specific individual. In S25, the CPU 8 first retrieves, from the RAM 9 or the HD 10, a reference filter corresponding to the identification number while the arbitrary person places his/her finger on the input end surface 3a of the FOP 3. Then, the arbitrary person manipulates the mode setting key to select the pattern pick up mode, whereupon the CPU 8 turns on the LEDs 2a and 2b. A fingerprint image is formed on the output end surface 3b of the FOP 3 and picked up by the CCD camera 4. The fingerprint image of the arbitrary person will be referred to as a "target fingerprint" hereinafter. The target fingerprint is digitized by the frame memory 5 and then stored in the frame memory 5. In this step, the target fingerprint is picked up only once, contrary to the step S21 of the filter storage process.

Next, in S26, the CPU 8 performs, in the frame memory 5, a fast Fourier transform on the target fingerprint in the same manner as in the filter storage process.

It is now assumed that the Fourier transformed target fingerprint TAG is expressed by the following equation (6):

$$TAG = X_t + Y_t j \tag{6}$$

In S27, the CPU 8 normalizes, into one (1), the amplitude term of the Fourier-transformed pattern TAG, thereby obtaining a phase-only pattern TAGpo of the Fourier-transformed pattern TAG.

The phase-only target pattern TAGpo can be expressed by the following formulas (7):

$$TAGpo = X_t / (X_t^2 + Y_t^2)^{1/2} + \{Y_t / (X_t^2 + Y_y^2)^{1/2}\} j$$
$$= X_t' + Y_t' j$$

amplitude=$(X_t'^2 + Y_t'^2)^{1/2} = 1$ phase=$\tan^{-1}(Y_t'/X_t') = \tan^{-1}(Y_t/X_t)$ \hfill (7)

Next, in the same manner as in the filter storage process, the CPU 8 further normalizes the target phase-only pattern TAGpo so that a power spectrum of the phase-only pattern will have a fixed total amount $N^2$.

The thus power-spectrum normalized fingerprint TAG"po is expressed by the following formulas (8):

$$TAG''po = \frac{X_t' \times (N \times N)}{TAGsum} + \frac{Y_t' \times (N \times N)}{TAGsum} j = X_t'' + Y_t'' j \tag{8}$$

where $$TAGsum = \sum_{n=1,m=1}^{N,N} \sqrt{(X_{tnm}^2 + Y_{tnm}^2)}$$

It is noted that the thus normalized phase-only pattern TAG"po will have a power spectrum with its total amount being fixed to the value $N^2$ as expressed by the following formula (9):

$$\sum_{n=1,m=1}^{N,N} \sqrt{\left[\left(\frac{X_{tnm} \times N^2}{TAGsum}\right)^2 + \left(\frac{Y_{tnm} \times N^2}{TAGsum}\right)^2\right]} \tag{9}$$

$$= \frac{N^2}{TAGsum} \sum_{n=1,m=1}^{N,N} \sqrt{(X_{tnm}^2 + Y_{tnm}^2)}$$

$$= \frac{N^2}{TAGsum} \times TAGsum$$

$$= N^2$$

Then, in S28, the CPU 8 multiplies the normalized target fingerprint TAG"po with the reference filter Multi* as expressed by the following formula (10):

$$Multi^* \cdot TAG''po = (X_M - Y_M j) \cdot (X_t'' + Y_t'' j) = (X_M \cdot X_t'' + Y_M \cdot Y_t'') + (X_M \cdot Y_t'' - X_t'' \cdot Y_M) j \tag{10}$$

Then, in S29, the CPU 8 performs an inverse Fourier transform on the multiplied result. The inverse Fourier-transformed result is a correlation image with a correlation representing the degree to which the reference fingerprint and the target fingerprint are similar to each other.

Then, in S30, the CPU 8 measures a highest amount of the correlation peak produced, and judges a match or a mismatch between the reference fingerprint and the target fingerprint. The CPU 8 then determines whether or not the arbitrary person is the specific person.

The judgement performed in S30 will be described below in greater detail.

The CPU 8 first calculates a power spectrum of the correlation image. The CPU 8 then measures a highest value "cp" of the correlation peak. The CPU 8 then performs a comparison calculation in a manner described below.

It is noted that the RAM 9 or the HD 10 previously stores a value "cp_cross" which is indicative of a maximum of correlation peaks for cross-correlations between different people. This value "cp_cross" is previously calculated through an experiment where cross-correlations are calculated for fingerprints of different people. It is preferable that quite a large number of different people be subjected to the experiment.

In order to leave a certain amount of margin between the value "cp_cross" and the correlation peak highest value "cp" obtained through S30, a safety rate "sr" may preferably be multiplied to the value "cp_cross." When desiring to leave a margin of 10%, for example, the safety rate "sr" is set to 1.1.

A match between the reference fingerprint and the target fingerprint is determined when the correlation peak highest value "cp" is higher than a product of the safety rate "sr" and the value "cp_cross." That is, match is determined when cp>cp_cross×sr. As a result, the arbitrary person is recognized as the specific person.

A mismatch is determined when the correlation peak highest value "cp" is equal to or lower than the product of the safety rate "sr" and the value "cp_cross." That is, mismatch is determined when cp≦cp_cross×sr. As a result, the arbitrary person is recognized as different from the specific person.

As described above, in the individual identification device of the present embodiment, the four reference fingerprints A, B, C, and D are superimposed on the reference filter to be used in the individual identification operation. Accordingly, even when the newly-picked up arbitrary person's fingerprint (target fingerprint) is somewhat rotated or distorted, the individual identification device will not falsely judge as a mismatch between the target fingerprint and the reference filter when the arbitrary person and the specific person are the same individual. The apparatus can therefore properly judge a match between identical person's fingerprints at an enhanced rate.

After performing the above-described judgement, the CPU 8 controls in S31 the display 6 to show the judged results. The CPU 8 further outputs a recognition signal 12, which represents whether or not the arbitrary person is the specific individual, to an external device, which performs various processes using the supplied recognition signal 12. The external device can be, for example, a door lock system provided to a door of a restricted area. The lock is released only when the recognition signal 12 represents that the arbitrary person is the specific person.

As described above, according to the individual identification apparatus of the present embodiment, the plurality of reference fingerprints are superimposed into the multiple reference filter. Individual identification operation is performed with using the thus prepared reference filter. Accordingly, even when the target fingerprint is picked up while being rotated out of its correct posture or distorted from its normal shape, if the arbitrary person is the specific person, the individual identification can properly recognize the arbitrary person as the specific person with an enhanced rate.

Additionally, the multiple filter can be produced through merely adding the Fourier-transformed results of the plurality of reference fingerprints. A short length of time is sufficient to produce the multiple filter. It is therefore possible to record the reference filter within a shorter period of time.

The apparatus performs a fast Fourier transform operation during the filter recordation process. Accordingly, the apparatus can record the reference filter within a quite short period of time.

Additionally, the apparatus 100 digitizes image signals, and electronically or digitally performs calculation operations with the use of several kinds of electronic devices. The stability and reliability of the apparatus is therefore high with regards to environmental changes such as temperature changes. The apparatus is easy to manufacture because the apparatus employs manufacturable electronic devices. The apparatus becomes compact and inexpensive because the apparatus does not employ any optical system for performing an optical correlation calculation.

In order to protect privacy of the specific person, conventionally it is necessary that the reference filter be coded before being stored in the apparatus. According to the apparatus 100 of the present embodiment, when the reference fingerprint is picked up by the CCD 4 at a resolution of 512×512 dots (pixels), the reference fingerprint may be converted into a rougher image with a lower resolution of 128×128 dots (pixels) so that insufficient information from the original reference fingerprint is retained to perform, for example, a minutiae-extracting type fingerprint identification operation. The apparatus 100 of the present embodiment can use such a rough reference fingerprint and still attain fingerprint identification with a high recognition accuracy.

Especially, because the apparatus of the present embodiment employs the phase-only type image correlation calculation operation, the apparatus Fourier-transforms the reference fingerprint and stores, as a reference filter, only a phase term of the Fourier-transformed reference fingerprint. Accordingly, the reference filter has no intensity information on the reference fingerprint. Thus, the apparatus of the present embodiment stores a highly-coded reference fingerprint which is very difficult to be reproduced into the original fingerprint.

Additionally, the apparatus of the present invention superimposes a plurality of reference fingerprints into the reference filter. The plurality of reference fingerprints are slightly different from one another in their rotational postures, shapes, and the like. Accordingly, it is very difficult to reproduce the original fingerprints from the reference filter.

As described above, the apparatus of the present embodiment employs the image correlation calculation method, in which a plurality of slightly-different reference fingerprints are picked up from a single specific person, the reference fingerprints are Fourier transformed, amplitude terms of the Fourier-transformed reference fingerprints are normalized, and then the phase terms of the Fourier-transformed reference fingerprints are superimposed into the multiple reference filter. The thus highly-coded reference filter can reliably protect the privacy of the specific person.

In the above description, the apparatus of the present embodiment employs the phase-only type image correlation calculation method. However, the device can employ a "phase-and-amplitude" type image correlation method.

Next, an explanation for the "phase-and-amplitude" type image correlation method will be provided.

The amplitudes of the Fourier-transformed plural reference fingerprints are not normalized into one (1), but are normalized, when required, so that their power spectrums will have a fixed total amount. Then, the Fourier-transformed plural reference fingerprints are added or superimposed one on another. Then, a complex conjugate of the superimposed pattern is calculated as a reference filter.

When desiring to identify an arbitrary person with the specific person, a target fingerprint of the arbitrary person is Fourier transformed, and multiplied with the reference filter. The multiplied result is inverse Fourier transformed into a correlation output. Match or mismatch between the arbitrary person and the specific person is determined based on the correlation output.

Thus, the individual identification operation can be achieved through both the phase-only type correlation calculation and the phase-and-amplitude type correlation calculation. It is noted, however, that a correlation, obtained through the phase-only type calculation, will have a sharper peak than does a correlation obtained through the phase-and-amplitude type calculation. The sharper correlation peak can perform a more reliable judgement on match and mismatch. Accordingly, the phase-only type calculation method can judge a match between identical persons and a mismatch between different people with a higher rate of success than does the phase-and-amplitude type calculation method.

The present inventor performed an experiment to compare the accuracy of the phase-only type calculation method and the phase-and-amplitude type calculation method. The experiment results confirm that the phase-only type method can determine a match between identical persons and a mismatch between different people with a higher rate than does the phase-and-amplitude type method.

As described already, the phase-only-filter is also advantageous in coding the reference filter.

The above embodiment describes a complex conjugate of the Fourier-transformed reference fingerprint as being multiplied with a Fourier-transformed target fingerprint to obtain a correlation output representing the degree to which the reference fingerprint and the target fingerprint are similar to each other. However, the Fourier-transformed reference fingerprint may be directly multiplied with the Fourier-transformed target fingerprint. In this case, the multiplied result is then inverse Fourier transformed and the inverse Fourier-transformed result is used as a correlation output indicative of similarity between the reference fingerprint and the target fingerprint. Then, a highest value of a correlation peak is measured and compared with the cross-correlation maximum value in the similar manner as described above. Whether or not the arbitrary person is the specific person is judged based on the compared result.

The above embodiment describes the plurality of reference fingerprints as being electronically Fourier transformed, whereupon the Fourier-transformed results are added or superimposed into the multiple filter. However, other various methods can be employed to produce the multiple filter. For example, the Fourier-transformed reference fingerprints may be superimposed one on another by: (1) calculating an average of the plural Fourier-transformed reference fingerprints; (2) subtracting the plural Fourier-transformed reference fingerprints from a predetermined value; or (3) calculating a root-mean-square value of the Fourier-transformed reference fingerprints.

Each of these steps (1)–(3) will be described below in greater detail (1) First, an average "AVE" of the Fourier-transformed reference fingerprints REF"po$_A$, REF"po$_B$, REF"po$_C$, and REF"po$_D$ is calculated. Then, a complex conjugate "AVE*" of the average value is calculated. The thus obtained complex conjugate "AVE*" serves as a multiple reference filter where the Fourier-transformed reference fingerprints are superimposed. The average value "AVE" and the conjugate "AVE*" can be expressed by the following formulas (11):

$$AVE = (REF''po_A + REF''po_B + REF''po_C + REF''po_D)/4 \quad (11)$$

$$= (X_A'' + X_B'' + X_C'' + X_D'')/4 +$$

$$(Y_A'' + Y_B'' + Y_C'' + Y_D'')j/4$$

$$= X_{AV} + Y_{AV}j$$

$$AVE^* = X_{AV} - Y_{AV}j$$

During the individual identification process, a target fingerprint TAG"po is obtained in the same manner as described previously. The target fingerprint TAG"po is multiplied with the reference filter AVE*, The multiplied result is inverse Fourier transformed into a correlation output which is indicative of similarity between the target fingerprint and the reference fingerprint.

(2) The Fourier-transformed reference fingerprints REF"po$_A$, REF"po$_B$, REF"po$_C$, and REF"po$_D$ are first subtracted from a predetermined standard value C. Then, a complex conjugate of an obtained result "SUB" is calculated. The thus obtained complex conjugate "SUB*" serves as a multiple reference filter where the Fourier-transformed reference fingerprints are superimposed. The subtracted result "SUB" and the complex conjugate "SUB*" can be expressed by the following formulas (12):

$$SUB = C - REF''po_A - REF''po_B - REF''po_C - REF''po_D \quad (12)$$

$$= (C_1 - X_A'' - X_B'' - X_C'' - X_D'') +$$

$$(C_2 - Y_A'' - Y_B'' - Y_C'' - Y_D'')j$$

$$= X_S + Y_Sj$$

$$SUB^* = X_S - Y_Sj$$

During the individual identification process, a target fingerprint TAG"po is obtained in the same manner as described previously. The target fingerprint TAG"po is multiplied with the reference filter SUB*. The multiplied result is inverse Fourier transformed into a correlation output which is indicative of similarity between the target fingerprint and the reference fingerprint.

(3) First, a root-mean-square value "RMS" of the Fourier-transformed reference fingerprints REF"po$_A$, REF"po$_B$, REF"po$_C$, and REF"po$_D$ is calculated. Then, a complex conjugate "RMS*" of the root-mean-square value is calculated. The thus obtained complex conjugate "RMS*" serves as a reference multiple filter on which the Fourier-transformed reference fingerprints are superimposed. The root-mean-square value "RMS" and the complex conjugate "RMS*" can be expressed by the following formulas (13):

$$RMS = \{REF''po_A^2 + REF''po_B^2 + REF''po_C^2 + \quad (13)$$

$$REF''po_D^2\}^{1/2}$$

$$= \{[(X_A''^2 - Y_A''^2) + (X_B''^2 - Y_B''^2) + (X_C''^2 - Y_C''^2) +$$

$$(X_D''^2 - Y_D''^2)] + [2X_A'' \cdot Y_A'' + 2X_B'' \cdot Y_B'' +$$

$$2X_C'' \cdot Y_C'' + 2X_D'' \cdot Y_D'']j\}^{1/2}$$

$$= X_R + Y_Rj$$

$$RMS^* = X_R - Y_Rj$$

During the individual identification process, a target fingerprint TAG"po is obtained in the same manner as described previously. The target fingerprint TAG"po is multiplied with the reference filter RMS*. The multiplied result is inverse Fourier transformed into a correlation output indicative of similarity between the target fingerprint and the reference fingerprint.

According to still another method for obtaining the multiple filter, a filter that has intermediate phase values among the plurality of Fourier-transformed reference fingerprints may be used as the multiple filter. For example, when four reference fingerprints are used as described above, a reference fingerprint that has the second or third largest phase values, may be used.

As described above, according to the present invention, a plurality of reference fingerprints are electronically superimposed into a multiple filter. Accordingly, the reference fingerprints can be recorded in the device within a short period of time. A correlation calculation is electronically achieved with the multiple filter. Even when the target fingerprint is somewhat rotated or distorted, the device can perform an accurate judgement with a high recognition rate.

While the invention has been described in detail with reference to the specific embodiment thereof, it would be apparent to those skilled in the art that various changes and modifications may be made therein without departing from the spirit of the invention.

In the above-described embodiment, the apparatus picks up fingerprints of the individuals, and calculates correlation between them. However, the apparatus can be modified to pick up other various body portions of the individuals and calculates correlation between them.

As described above, in the individual identification apparatus of the present invention, the image pick up portion picks up a pattern of a predetermined body portion of a specific individual a plurality of times and outputs a plurality of reference image signals for being stored. The image pick up portion also picks up a pattern of the predetermined body portion of an arbitrary individual and outputs a target image signal. The calculation processing portion electronically performs a Fourier transform on the plurality of reference image signals and the target image signal. The calculation processing portion superimposes the Fourier transformed results of the plurality of reference image signals. The calculation processing portion electronically multiplies the thus superimposed reference image signals with the Fourier transformed target image signal. The calculation processing portion electronically performs an inverse Fourier transform on the multiplied result, to thereby obtain a similarity degree output indicative of similarity between the target image signal and the reference image signals. Based on the thus obtained similarity degree output, the calculation processing portion judges whether or not the arbitrary individual and the specific individual are the same individual.

In order to electronically multiply the superimposed reference image signals with the Fourier transformed target image signal, the superimposed reference image signals may preferably be multiplied with a complex conjugate of the Fourier transformed target image signal. Or otherwise, the superimposed reference image signals may be multiplied with the Fourier transformed target image signal.

Thus, according to the present invention, the plurality of reference images are electronically Fourier transformed and then superimposed into a reference multiple filter. A correlation calculation is electronically achieved with the use of the thus obtained multiple filter. Thus, the Fourier-transformed reference images may be simply superimposed on the reference filter. It becomes unnecessary to perform correlation calculations a plurality of times. Accordingly, the reference images can be recorded within a short period of time. Additionally, the apparatus electronically performs correlation calculations with the use of several kinds of electronic devices. The stability and reliability of the apparatus becomes high with regards to environmental changes such as temperature changes. The apparatus is also easy to manufacture, compact, and inexpensive, while maintaining high accuracy. Because the apparatus does not employ any optical correlation calculating system, the apparatus can be made compact.

According to the embodiment, the calculation processing portion superimposes the plurality of the Fourier-transformed reference image signals through electronically adding the Fourier-transformed reference image signals with one another. Alternatively, the calculation processing portion may superimpose the plurality of the Fourier-transformed reference image signals through electronically calculating an average of the Fourier-transformed reference image signals. The calculation processing portion may superimpose the plurality of the Fourier-transformed reference image signals through electronically subtracting the Fourier-transformed reference image signals from a predetermined standard value. The calculation processing portion may superimpose the plurality of the Fourier-transformed reference image signals through electronically calculating a root-mean-square value of the Fourier-transformed reference image signals.

Further, the calculation processing portion may normalize an amplitude of each of the plurality of Fourier-transformed reference image signals before superimposing the plurality of Fourier-transformed reference image signals into the multiple filter. The calculation processing portion may normalize an amplitude of the Fourier-transformed target image signal before multiplying the Fourier-transformed target image signal with the multiple filter.

Through the normalizing process of the reference image signals, intensity information on the reference images is neglected. It is difficult to reproduce the original pattern of the specific person's body portion from the reference image signals so the privacy of the specific person can be reliably protected.

Also, the calculation processing portion may normalize the plurality of Fourier-transformed reference image signals so that the Fourier-transformed reference image signals will have power spectrums of a fixed total value. The calculation processing portion may perform this normalization operation before superimposing the plurality of Fourier-transformed reference image signals into the multiple filter.

The calculation processing portion may further normalize the Fourier-transformed target image signal so that the Fourier-transformed target image signal will have a power spectrum of a fixed total value. The calculation processing portion may perform this normalization operation before multiplying the Fourier-transformed target image signal with the multiple filter.

Accordingly, judgement can be achieved under a fixed condition which is free from the variety of the picked-up images. Accordingly, the apparatus can perform a stable individual identification operation.

What is claimed is:

1. An individual identification apparatus for identifying an arbitrary individual with a specific individual, the apparatus comprising:

image pick up means for picking up a pattern of a predetermined body portion of a specific individual a plurality of times and for outputting a plurality of reference image signals for being stored, the image pick up means also picking up, a single time, a pattern of the predetermined body portion of an arbitrary individual desired to be identified with the specific individual and for outputting a single target image signal; and calculation processing means for electronically performing a Fourier transform on the plurality of reference image signals to obtain a plurality of Fourier transformed reference image signals, each Fourier transformed reference image signal being represented by a first complex indication, electronically performing a Fourier transform on the single target image signal to obtain a single Fourier transformed target image signal represented by a second complex indication, for superimposing the plurality of Fourier transformed reference image signals into a multiple filter indicated by a third complex indication, for electronically multiplying the multiple filter with the single Fourier transformed target image signal, and for electronically performing an inverse Fourier transform on the multiplied result to thereby obtain a similarity degree output indicative of similarity between the reference image signals and the single target image signal, thereby judging whether or not the arbitrary individual and the specific individual are the same individual.

2. An individual identification as claimed in claim 1, wherein the calculation processing means superimposes the plurality of the Fourier-transformed reference image signals through electronically adding the Fourier-transformed reference image signals.

3. An individual identification as claimed in claim 1, wherein the calculation processing means superimposes the plurality of the Fourier-transformed reference image signals through electronically calculating an average of the Fourier-transformed reference image signals.

4. An individual identification as claimed in claim 1, wherein the calculation processing means superimposes the plurality of the Fourier-transformed reference image signals through electronically subtracting the Fourier-transformed reference image signals from a predetermined standard value.

5. An individual identification as claimed in claim 1, wherein the calculation processing means superimposes the plurality of the Fourier-transformed reference image signals through electronically calculating a root-mean-square value of the Fourier-transformed reference image signals.

6. An individual identification as claimed in claim 1, wherein the calculation processing means normalizes an amplitude of each of the plurality of Fourier-transformed reference image signals before superimposing the plurality of Fourier-transformed reference image signals into the multiple filter, the calculation processing means normalizing an amplitude of the Fourier-transformed target image signal before multiplying the Fourier-transformed target image signal with the multiple filter.

7. An individual identification as claimed in claim 1, wherein the calculation processing means normalizes each of the plurality of Fourier-transformed reference image signals so that the Fourier-transformed reference image signal will have a power spectrum of a fixed total value before superimposing the plurality of Fourier-transformed reference image signals into the multiple filter, the calculation processing means normalizing the Fourier-transformed target image signal so that the Fourier-transformed target image signal will have a power spectrum of a fixed total value before multiplying the Fourier-transformed target image signal with the multiple filter.

8. An individual identification apparatus as claimed in claim 1, wherein the calculation processing means includes:

Fourier transform means for electronically performing a Fourier transform on the plurality of reference image signals to obtain a plurality of Fourier transformed reference patterns, the first complex indication representing each Fourier transformed reference pattern and having both an amplitude term and a phase term, and for electronically performing a Fourier transform on the single target image signal to obtain a single Fourier transformed target pattern, the second complex indication representing the single Fourier transformed target pattern and having both an amplitude term and a phase term;

superimposing means for electronically superimposing at least the phase terms of the plurality of Fourier transformed reference patterns into the multiple filter;

multiplying means for electronically multiplying the multiple filter with at least the phase term of the single Fourier transformed target image signal;

inverse Fourier transform means for electronically performing the inverse Fourier transform on the multiplied result to thereby obtain a similarity degree output indicative of similarity between the reference image signals and the single target image signal, thereby judging whether or not the arbitrary individual and the specific individual are the same individual.

9. An individual identification as claimed in claim 8, wherein:

in said Fourier transform means, each Fourier transformed reference pattern is defined by a corresponding real part and a corresponding imaginary part, and the single Fourier transformed target pattern is defined by a corresponding real part and a corresponding imaginary part;

the multiple filter is defined by a corresponding real part and a corresponding imaginary part; and said multiplying means electronically multiplies the multiple filter with the single Fourier transformed target image signal.

10. An individual identification apparatus as claimed in claim 9, wherein the superimposing means includes:

first normalizing means for electronically normalizing the amplitude term of each Fourier transformed reference pattern, thereby obtaining a phase-only Fourier transformed reference pattern for each reference pattern:

second normalizing means for electronically normalizing each phase-only Fourier transformed reference pattern so that a power spectrum of each phase-only Fourier transformed reference pattern will have a fixed total amount; and filter producing means for producing the multiple filter based on all the phase-only Fourier transformed reference patterns normalized by the second normalizing means.

11. An individual identification apparatus as claimed in claim 10, wherein the multiplying means includes:

third normalizing means for electronically normalizing the amplitude term of the single Fourier transformed target pattern, thereby obtaining a single phase-only Fourier transformed target pattern;

fourth normalizing means for electronically normalizing the single phase-only Fourier transformed target pattern so that a power spectrum of the single phase-only Fourier transformed target pattern will have a fixed total amount; and multiplication means for electronically multiplying the multiple filter with the single phase-only Fourier transformed target pattern that has been normalized by the fourth normalizing means.

12. An individual identification apparatus as claimed in claim 11, wherein the superimposing means further includes:

adding means for electronically adding all the phase-only Fourier transformed reference patterns normalized by the second normalizing means; and conjugate calculating means for electronically calculating a conjugate of the added result, thereby obtaining the multiple filter.

13. An individual identification apparatus as claimed in claim 11, wherein the superimposing means further includes:

average calculating means for electronically calculating an average of all the phase-only Fourier transformed reference patterns normalized by the second normalizing means; and conjugate calculating means for electronically calculating a conjugate of the average, thereby obtaining the multiple filter.

14. An individual identification apparatus as claimed in claim 11, wherein the superimposing means further includes:

subtracting means for electronically subtracting, from a predetermined standard value, all the phase-only Fourier transformed reference patterns normalized by the second normalizing means; and conjugate calculating means for electronically calculating a conjugate of the subtracted result, thereby obtaining the multiple filter.

15. An individual identification apparatus as claimed in claim 11, wherein the superimposing means further includes:

root-mean-square calculating means for electronically calculating a root-mean-square for all the phase-only Fourier transformed reference patterns normalized by the second normalizing means; and conjugate calculating means for electronically calculating a conjugate of the root-mean-square, thereby obtaining the multiple filter.

16. An individual identification as claimed in claim 8, wherein the image pick up means outputs a plurality of reference image signals so that each reference image signal is a two-dimensional image having a size of N×N dots, and outputs the single target image signal so that the target image signal is another two-dimensional image having a size of N×N dots, wherein:

with respect to said Fourier transform means, each Fourier transformed reference pattern is defined by a formula of $(X_r+Y_r j)$ where $X_r$ is a corresponding real part and $Y_r$ is a corresponding imaginary part, each of the values $X_r$ and $Y_r$ being a matrix consisting of N×N values, and the single Fourier transformed target pattern is defined by a formula of $(X_t+Y_t j)$ where $X_t$ is a corresponding real part and $Y_t$ is a corresponding imaginary part, each of the values $X_r$ and $Y_r$ being a matrix consisting of N×N values;

the multiple filter is defined by a formula of $(X+Yj)$ where X is a corresponding real part and Y is a corresponding imaginary part; and in said multiplying means the multiple filter is electronically multiplied with the single Fourier transformed target image signal.

17. An individual identification apparatus as claimed in claim 16 wherein the superimposing means includes:

first normalizing means for electronically normalizing an amplitude term of each Fourier transformed reference pattern $(X_r+Y_r j)$, thereby obtaining a phase-only Fourier transformed reference pattern $(X_r'+Y_r'j)$ for each reference pattern where $X_r'=X_r/(X_r^2+Y_r^2)^{1/2}$ and $Y_r'=Y_r/(X_r^2+Y_r^2)^{1/2}$;

second normalizing means for electronically normalizing each phase-only Fourier transformed reference pattern into a normalized phase-only Fourier transformed reference pattern $(X_r''+Y_r''j)$ where $Xr''=X_r'\times(N\times N)/\text{REFsum}$, $Y_r''=Y_r'\times(N\times N)/\text{REFsum}$, and $$REFsum = \sum_{n=1,m=1}^{N,N} \sqrt{(X^2 nm + Y^2 nm)}$$

so that a power spectrum of each phase-only Fourier transformed reference pattern will have a fixed total amount of $N^2$; and filter producing means for producing the multiple filter $(X+Yj)$ based on all the normalized phase-only Fourier transformed reference patterns $(X_r''+Y_r''j)$.

18. An individual identification apparatus as claimed in claim 17, wherein the multiplying means includes:

third normalizing means for electronically normalizing an amplitude term of the single Fourier transformed target pattern $(X_{t+Yt}j)$, thereby obtaining a phase-only Fourier transformed target pattern $(X_t'+Y_t'j)$ where $X_t'=X_t/(X_t^2+Y_t^2)^{1/2}$ and $Y_t'=Y_t/(X_t^2+Y_t^2)^{1/2}$;

fourth normalizing means for electronically normalizing the single phase-only Fourier transformed target pattern into a normalized phase-only Fourier transformed target pattern $(X_t''+Y_t''j)$ where $X_t''=X_t'\times(N\times N)/\text{TAGsum}$, $Y_t''=Y_t'\times(N\times N)/\text{TAGsum}$, and $$TAGsum = \sum_{n=1,m=1}^{N,N} \sqrt{(Xt^2 nm + Yt^2 nm)}$$

so that a power spectrum of the phase-only Fourier transformed target pattern will have the fixed total amount of $N^2$; and multiplication means for electronically multiplying the multiple filter $(X+Yj)$ with the single normalized phase-only Fourier transformed target pattern $(X_t''+Y_t''j)$, thereby producing a multiplied result of $(X\cdot X_t''+Y\cdot Y_t'')+(X\cdot Y_t''-Y\cdot X_t'')j$.

19. An individual identification apparatus as claimed in claim 18, wherein the superimposing means further includes:

adding means for electronically adding all the normalized phase-only Fourier transformed reference patterns into a sum defined by $(\Sigma X_r'')+(\Sigma Y_r'')j$; and conjugate calculating means for electronically calculating a conjugate $(\Sigma X_r'')-(\Sigma Y_r'')j$ of the added result, thereby obtaining the multiple filter.

20. An individual identification apparatus as claimed in claim 18, wherein the superimposing means further includes:

average calculating means for electronically calculating an average $(\Sigma X_r''/M)+(\Sigma Y_r''/M)j$ of all the normalized phase-only Fourier transformed reference patterns $(X_r+Y_r j)$ where M is the total number of the reference patterns; and conjugate calculating means for electronically calculating a conjugate $(\Sigma X_r''/M)-(\Sigma Y_r''/M)j$ of the average, thereby obtaining the multiple filter.

21. An individual identification apparatus as claimed in claim 18, wherein the superimposing means further includes:

subtracting means for electronically subtracting, from a predetermined standard value $C_1+C_2 j$, all the normalized phase-only Fourier transformed reference patterns, thereby obtaining a subtracted result of $(C_1-\Sigma X_r'')+(C_2-\Sigma Yr'')j$; and conjugate calculating means for electronically calculating a conjugate $(C_1-\Sigma X_r'')-(C_2-\Sigma Yr'')j$ of the subtracted result, thereby obtaining the multiple filter.

22. An individual identification apparatus as claimed in claim 18, wherein the superimposing means further includes:

root-mean-square calculating means for electronically calculating a root-mean-square, $[\Sigma(X_r''^2-Y_r''^2)+\Sigma(2X_r''Y_r'')]^{1/2}$, of all the normalized phase-only Fourier transformed reference patterns $X_r''+Y_r''j$; and conjugate calculating means for electronically calculating a conjugate of the average $[\Sigma(X_r''^2-Y_r''^2)+\Sigma(2X_r''Y_r'')]^{1/2}$, thereby obtaining the multiple filter.

* * * * *